US009436799B2

(12) United States Patent
McCoy et al.

(10) Patent No.: US 9,436,799 B2
(45) Date of Patent: Sep. 6, 2016

(54) SYSTEMS AND METHODS FOR REMOTE IMAGE RECONSTRUCTION

(75) Inventors: Daniel McCoy, Whitefish Bay, WI (US); Vinod Palathinkara, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 272 days.

(21) Appl. No.: 13/561,508

(22) Filed: Jul. 30, 2012

(65) Prior Publication Data

US 2014/0029818 A1 Jan. 30, 2014

(51) Int. Cl.
| G06K 9/00 | (2006.01) |
| A61B 6/00 | (2006.01) |
| G01N 23/00 | (2006.01) |
| G21K 1/12 | (2006.01) |
| H05G 1/60 | (2006.01) |
| G01N 23/04 | (2006.01) |
| G06F 19/00 | (2011.01) |
| G06T 11/00 | (2006.01) |
| A61B 5/05 | (2006.01) |
| G06Q 10/00 | (2012.01) |
| G06Q 50/00 | (2012.01) |

(52) U.S. Cl.
CPC ........... *G06F 19/321* (2013.01); *G06F 19/328* (2013.01); *G06T 11/003* (2013.01)

(58) Field of Classification Search
None
See application file for complete search history.

(56) References Cited

U.S. PATENT DOCUMENTS

| 5,801,755 | A | 9/1998 | Echerer |
| 5,862,223 | A | 1/1999 | Walker et al. |
| 6,006,191 | A | 12/1999 | DiRienzo |
| 6,113,450 | A | 9/2000 | Narayanan et al. |
| 6,206,829 | B1 | 3/2001 | Iliff |
| 6,283,761 | B1 | 9/2001 | Joao |
| 6,418,346 | B1 | 7/2002 | Nelson et al. |
| 6,678,703 | B2 | 1/2004 | Rothschild et al. |
| 6,829,378 | B2 | 12/2004 | DeFilippo et al. |
| 6,988,074 | B2 * | 1/2006 | Koritzinsky et al. ............. 705/2 |
| 7,357,312 | B2 | 4/2008 | Gangi |
| 7,657,560 | B1 | 2/2010 | DeRienzo |
| 8,488,013 | B2 * | 7/2013 | Jia et al. .................. 348/211.99 |
| 2001/0041991 | A1 | 11/2001 | Segal et al. |
| 2002/0016718 | A1 | 2/2002 | Rothschild et al. |
| 2002/0019751 | A1 | 2/2002 | Rothschild et al. |
| 2002/0095313 | A1 | 7/2002 | Haq |
| 2002/0149617 | A1 | 10/2002 | Becker |
| 2002/0164059 | A1 * | 11/2002 | DiFilippo et al. ............ 382/128 |
| 2003/0069897 | A1 * | 4/2003 | Roy et al. .................. 707/104.1 |

(Continued)

*Primary Examiner* — Matthew Bella
*Assistant Examiner* — Jose M Torres
(74) *Attorney, Agent, or Firm* — Dean D. Small; The Small Patent Law Group, LLC.

(57) ABSTRACT

A system is provided including a processing unit including an input module, a processing module, and an output module. The processing unit is located at a first location that is remotely located from a scanning location at which a remote medical scanning system is located. The input module is configured to communicate with the remote medical scanning system to receive scanning data obtained during a scan performed by the remote medical scanning system, the scanning data corresponding to an object scanned by the remote medical scanning system. The processing module is configured to use the scanning data to reconstruct an image representing the object. The output module is configured to provide access to the image reconstructed by the processing module to at least one of the remote medical scanning system or a requester located remotely from the first location.

27 Claims, 5 Drawing Sheets

(56) References Cited

U.S. PATENT DOCUMENTS

| | | |
|---|---|---|
| 2003/0181804 A1* | 9/2003 | Gagnon et al. ............... 600/410 |
| 2005/0159985 A1 | 7/2005 | Bertram |
| 2005/0234742 A1 | 10/2005 | Hodgdon |
| 2005/0251006 A1* | 11/2005 | Dellis ........................... 600/407 |
| 2006/0184524 A1 | 8/2006 | Pollanz |
| 2006/0195342 A1 | 8/2006 | Khan et al. |
| 2006/0282287 A1 | 12/2006 | McKinley et al. |
| 2007/0124169 A1* | 5/2007 | Irving et al. ...................... 705/2 |
| 2008/0126119 A1 | 5/2008 | Sirohey et al. |
| 2008/0126120 A1 | 5/2008 | Sirohey et al. |
| 2008/0126121 A1 | 5/2008 | Sirohey et al. |
| 2008/0181471 A1* | 7/2008 | Chung et al. ................. 382/128 |
| 2009/0123048 A1* | 5/2009 | Leroux et al. ................ 382/131 |
| 2011/0081065 A1* | 4/2011 | Canstein ....................... 382/131 |
| 2012/0089015 A1* | 4/2012 | Gagnon et al. ............... 600/425 |
| 2013/0208955 A1* | 8/2013 | Zhao .................... G06F 19/321 382/128 |

\* cited by examiner

SYSTEMS AND METHODS FOR REMOTE IMAGE RECONSTRUCTION

BACKGROUND OF THE INVENTION

The subject matter disclosed herein relates generally to image reconstruction, and more particularly to systems and methods for remote image reconstruction.

Images of a subject, for example aspects of interest of a patient, may be obtained by a variety of different methods. Such methods include, as examples, single photon emission computed tomography (SPECT), positron emission tomography (PET), magnetic resonance imaging (MRI), and computed tomography (CT). These imaging systems typically form an image by performing one or more data acquisitions at discrete time intervals, with an image formed from a combination of the information obtained by the data acquisitions. For example, nuclear medicine (NM) imaging systems use one or more image detectors to acquire imaging data, such as gamma ray or photon imaging data. The image detectors may be, for example, gamma cameras that acquire a view or views of emitted radionuclides (from an injected radioisotope) from a patient being imaged.

After the imaging data is acquired, one or more processing steps are performed to reconstruct an image using the imaging data. This processing may be quite intensive in nature, and may require significant processing capability. Conventional processing systems are located proximate to the image acquisition site. For example, a processor or workstation typically is associated with an operator's console or other unit and dedicated to a particular image acquisition device. Thus, conventional scanning and reconstructing of images require considerable resources expended for the hardware required on-site for each dedicated workstation with processing capabilities. Further, such systems are often difficult and inconvenient to update. For example, each time a software update is to be implemented (for example, to update or otherwise change the software for reconstructing images), the software must be uploaded on-site in field, requiring the expense and inconvenience of using a field technician, as well as resulting in downtime of the processor and associated scanning equipment during the update. Also, each time software is updated for a particular console or workstation, a costly and timely regulatory approval process must be performed for the particular software and device combination. For example, the approval process may be required for each particular storage and device type combination. By updating the software for such a combination, the entire operating software of the device is essentially updated, and regulatory approval for the updated particular storage and device type combination is required. Further still, due at least in part to limited storage as well as difficulty in updating, and the initial expense associated with acquiring a given software product for image reconstruction, current systems typically provide a very limited range of options of software available for processing, thereby limiting different types and/or levels of detail of processing available for a given imaging device. Yet further still, typical on-site consoles are generally configured to only accept a limited amount of software, and compatibility issues prevent certain consoles (for example, from a first manufacturer or provider) from utilizing certain software (for example, from a second manufacturer or provider). Thus, certain presently known image reconstruction systems or methods are difficult to update, limited in performance, and require costly equipment, both in terms of initial purchase and also in terms of maintenance and updating.

BRIEF DESCRIPTION OF THE INVENTION

In accordance with various embodiments, a system is provided. The system includes a processing unit including an input module, a processing module, and an output module. The processing unit is located at a first location that is remotely located from a scanning location at which a remote medical scanning system is located. The input module is configured to communicate with the remote medical scanning system to receive scanning data obtained during a scan performed by the remote medical scanning system, the scanning data corresponding to an object scanned by the remote medical scanning system. The processing module is configured to use the scanning data to reconstruct an image representing the object using a processing technique selected from a plurality of processing techniques available to the processing module. The plurality of techniques includes a plurality of sub-groups of techniques that relate to a corresponding plurality of imaging modalities. The output module is configured to provide access to the image reconstructed by the processing module to at least one of the remote medical scanning system or a requestor located remotely from the first location.

In accordance with other embodiments, a method for reconstructing an image is provided. The method includes receiving, at a processing center located at a first location, scanning data from a medical scanning system located at a second location. The first location and the second location are remote from each other. Also, the method includes selecting, via a processing module of the processing center, a processing technique from a plurality of processing techniques available to the processing module. The plurality of techniques includes a plurality of sub-groups of techniques relating to a corresponding plurality of imaging modalities. The method also includes reconstructing an image at the processing center using the scanning data from the medical scanning system and the selected processing technique. Further, the method also includes providing access to the image reconstructed at the processing center to at least one of the medical scanning system or a requestor located remotely from the processing center.

In accordance with yet other embodiments, a tangible and non-transitory computer readable medium including one or more computer software modules is provided. The computer readable medium is configured to direct a processor to receive, at a processing center located at a first location, scanning data from a medical scanning system located at a second location. The first location and the second location are remote from each other. The computer readable medium is further configured to direct the processor to select, via a processing module of the processing center, a processing technique from a plurality of processing techniques available to the processing module. The plurality of techniques includes a plurality of sub-groups of techniques relating to a corresponding plurality of imaging modalities. The computer readable medium is also configured to direct the processor to reconstruct an image at the processing center using the scanning data from the medical scanning system and the selected processing technique. Further, the computer readable medium is configured to direct a processor to provide access to the image reconstructed at the processing center to at least one of the medical scanning system or a requestor located remotely from the processing center.

DETAILED DESCRIPTION OF THE INVENTION

Figure 1:
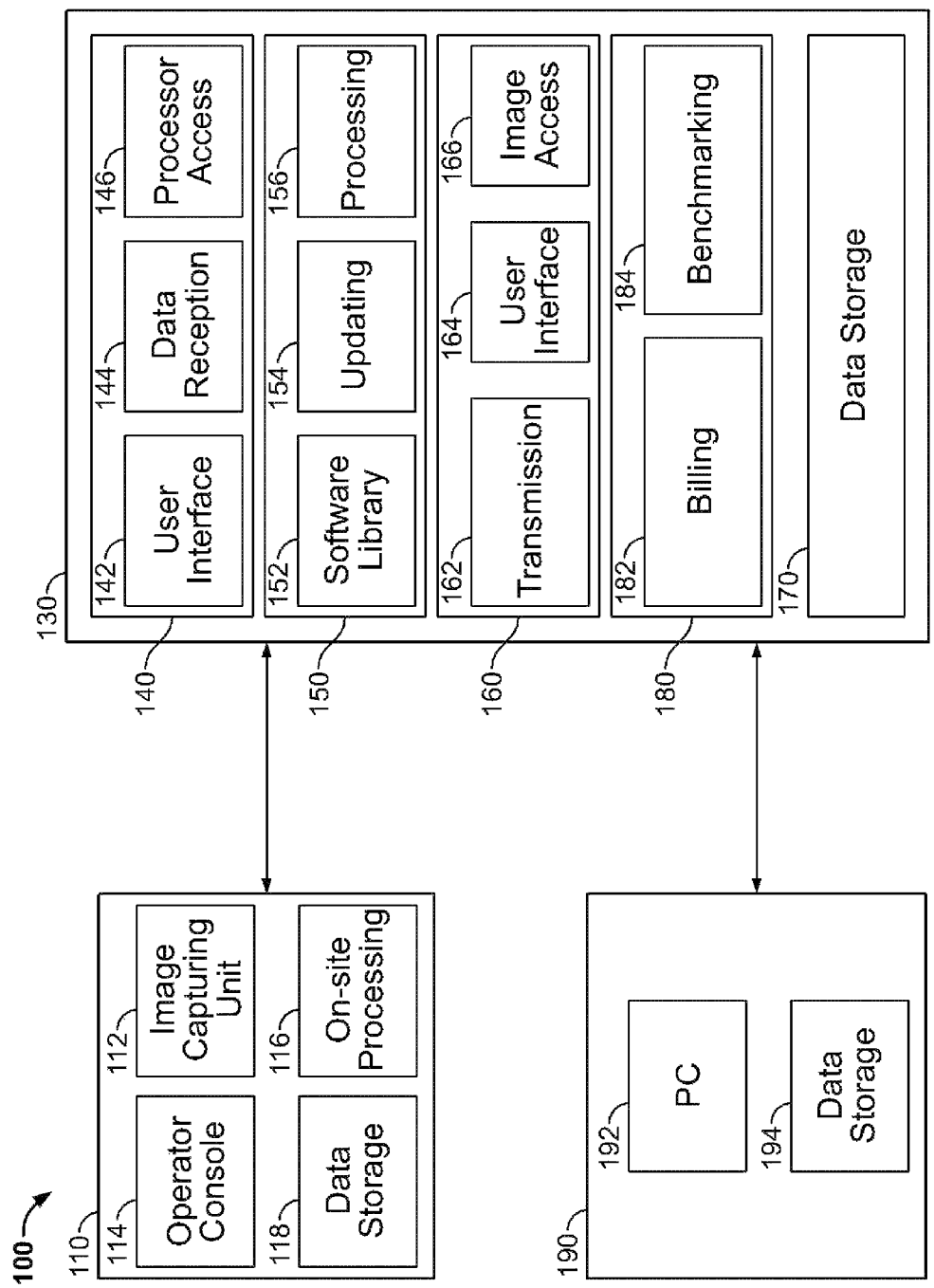
FIG. 1 is a block diagram of an imaging system in accordance with various embodiments.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrases "image" or "reconstructing an image" are not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image.

Various embodiments provide systems and methods for remote or centralized processing of image information to reconstruct images using data acquired during scans. In certain embodiments, image information acquired at a first location is forwarded to a second location remote from the first location for reconstructing an image based on the acquired image information from the first location. For example, information acquired by a medical scanning system may be transmitted to a centralized processing center that is also in communication with a plurality of additional remote medical scanning systems from which the centralized processing center may also receive image information for different scanning processes or procedures. For example, a processing center may communicate with a plurality of medical scanning systems via a cloud arrangement. The processing center may provide a shared or centralized processing, a shared or centralized software repository, or a combination thereof.

Embodiments allow for centralized processing that removes or reduces requirements for expensive on-site equipment, time-consuming on-site update procedures, or costly and time-consuming regulatory validations for each particular on-site processing device. Instead, for example, the centralized processing center in various embodiments may be updated and validated for regulatory purposes, thereby replacing a large number of regulatory validations with a single regulatory validation. For example, as discussed above, the approval process may be required for each particular storage and device type combination of known systems. By updating the software for such a combination, the entire operating software of the device for known systems is essentially updated, and regulatory approval for the updated particular storage and device type combination is required. Various embodiments effectively break the link between the operating components of software and the processing components of software so that updates to processing techniques need not require effective updates to operating software and attendant required regulatory validation. Embodiments also provide for convenient updating so that a plurality of scanning systems may have access to state of the art processing techniques without requiring on-site updating. Further still, embodiments provide for reception and processing of data in a standardized format, thereby alleviating compatibility issues between software and devices of different providers.

Embodiments also reduce the need for licensing multiple users and devices at a single scanning system or systems associated with a given user, as one identification may suffice for all users associated with a given entity, such as a hospital, clinic, or research facility. Also, in embodiments, more than one viewer at a time may access reconstructed images. Further, embodiments also provide for improved training, as the centralized processing center may also serve as a repository for training materials accessible by users. Yet further still, various embodiments training requirements are greatly reduced or effectively eliminated, as a user's software (e.g. for operating the user's equipment) may be generally unchanged, with the user only needing to know what options are available to choose from in requesting a desired image reconstruction option. Further still, embodiments track processing technique selections by a variety of users and entities, and provide information regarding the types of processing selected for comparable scanning procedures or acquired data, thereby providing a benchmarking functionality. Yet further still, embodiments provide a user with a preview of a scanning process, allowing a user to select a different mode of processing or additional features of processing if the preview indicates the image will not be satisfactory, reducing or preventing a need for re-processing and/or re-scanning due to unsatisfactory images.

Various embodiments provide reconstruction on a subscription basis. Thus, in embodiments, ownership of, for example, a given software used for a reconstructing an image, is shifted from a user or health provider to a manufacturer or software provider, with access to the given software effectively rented instead of purchased. Further still, embodiments provide for improved non-obsolescence of technology. For example, with certain known systems a user that buys a piece of software owns that piece of software for the entire future. When the software becomes obsolete, the user still owns the now obsolete software. In contrast, various embodiments provide for access right away to updated and/or new software. For example, an initial release of a software, (e.g. "v1") may be provided at a first time. At a subsequent time, a new feature set (for example, improved processing and/or improved user interaction capabilities) may be released. With known systems, it may cost prohibitive to download and/or validate the new version on an old computer system using "v1." Various embodiments provide for near instantaneous access to such updates without the requirement for downloading and/or validation at the user's site.

For example, a user or entity may pay a flat fee on a periodic basis, such as monthly, for unlimited processing for a period of time, for unlimited processing by a bundle or subset of available processing techniques, or for a given amount of processing on a periodic basis, for example a given number of scans or a given amount of processing time. Additionally or alternatively, embodiments allow a user to pay a one-time or other finite occurrence fee, for example, for processing techniques that are not commonly utilized (such as, for example, 5 reconstructions by a given processing technique, or as another example, 10 reconstructions by any one technique or combinations of techniques). Thus, a processing technique that is not used frequently enough to justify the initial outlay for required on-site hardware and software may be made available to a user or entity on an as-required basis without the cost-prohibitive initial outlay or update or maintenance costs associated with on-site processing. Embodiments also provide for centralized processing on a trial or free basis for a limited number of images and/or improved education, training, and use of newly updated image reconstruction software. Further still, various embodiments provide for a direct, nearly immediate process by which a user may acquire access to a processing technique. In contrast to known systems that require, for example, placement of an order with a sales representative, waiting for installation, and further training, various embodiments provide for a user to be able to purchase and nearly immediately use a given processing technique.

A technical effect of at least one embodiment is improving image quality, for example, by providing a user access to an increased variety of image reconstruction software, appropriate software for a particular scan and associated acquired data, and/or improved access to the most recent and up to date software and/or processing techniques. Additionally, a technical effect of at least one embodiment is reduced initial expense and reduced maintenance expense associated with on-site scanning systems. A further technical effect of at least one embodiment is improvement of access to up-to-date processing techniques. Also, a technical effect of at least one embodiment is reduced time and expense for regulatory validation associated with scanning and image reconstruction. A further technical effect of at least one embodiment is ameliorating compatibility issues between scanning devices and image reconstruction software.

FIG. 1 provides a block diagram of an imaging system 100 in accordance with various embodiments. The imaging system 100 includes a medical scanning system 110, a processing center 130, and remote viewing system 190. In the illustrated embodiment, the medical scanning system 110 is configured to perform a scan of an object, for example an aspect or region of interest of a patient, and to acquire imaging data during the scan. The imaging data acquired during the scan may then be transmitted to the processing center 130, where an image representing the object scanned is reconstructed using the imaging data transmitted from the medical scanning system 110. The remote viewing system 190 is configured to receive or otherwise access a reconstructed image from the processing center 130 for viewing. The remote viewing system 190 may, for example, be a workstation or a simple PACS system. In embodiments, the remote viewing system 190 and the medical scanning system 110 may share features in common. In embodiments, some or all of image reconstruction processing may be performed using the remote viewing system 190.

For simplicity and clarity, in the illustrated embodiments, only one of each of the medical scanning system 110, processing center 130, and remote viewing system 190 are depicted. In embodiments, a plurality of one or more medical scanning systems 110, processing centers 130, and remote viewing systems 190 may be present. For example, one processing center may be associated with a plurality of medical scanning systems 110 and remote viewing systems 190. In other embodiments, a plurality of processing centers 130 may be employed, for example with each processing center 130 having a corresponding type of processing to be performed, geographical location, and/or customer base associated therewith, with each of the processing centers 130 having associated therewith a plurality of medical scanning systems 110 and remote viewing systems 190. Further, in embodiments, some or all of the medical scanning systems 110 may comprise a viewing system substantially similar to the remote viewing system 190.

In the particular embodiment depicted in FIG. 1, each of the medical scanning system 110, the processing center 130, and the remote viewing system 190 are located remotely from each other. Components or systems may be considered as remote from each other, for example, when not located in general physical proximity to each other. For example, components or systems that are physically located at different locations, for example not within the same facility (such as a hospital), may be considered remote. As another example, remote locations may be administered by different parties or entities. As still another example, in embodiments, systems that are remote from each other may be accessible by different parties. For example, a scanning system may be located at a facility administered by a customer (e.g. a hospital or clinic) and physically accessible to the customer only, while a processing center may be located at a facility administered by a provider (e.g. a provider of scanning equipment and/or software) and physically accessible to the provider only. In embodiments, not all of the various components or systems may be remotely located from each other. For example, the medical scanning system 110 and the remote viewing system 190 may be located in physical proximity to each other and located in the same facility, while the processing center 130 is remotely located from both the medical scanning system 110 and the remote viewing system 190. In embodiments, the remote viewing system 190 and the medical scanning system 110 may be integrated.

The medical scanning system 110 includes an image capturing unit 112, an operator console 114, an on-site processing module 116, and a data storage module 118. The image capturing unit 112 is operated under control of the operator console 114 to allow a practitioner or other operator to administer a scan. Data gathered during the scan is saved in the data storage module 118.

The image capturing unit 112 is configured to acquire data of an object, such as a patient or a portion, region, or aspect of a patient. The image capturing unit 112 may be, for example, a unit configured to capture images by a technique such as single photon emission computed tomography (SPECT), positron emission tomography (PET), magnetic resonance imaging (MRI), and computed tomography (CT). One or more data acquisitions by the image capturing unit 112 may be performed at discrete time intervals. By way of example, the image capturing unit 112 may be a gamma camera associated with a nuclear medicine (NM) imaging system that is configured to acquire imaging data, such as gamma ray or photon imaging data. Such a gamma camera may acquire a view or views of emitted radionuclides (from an injected radioisotope) from a patient being imaged.

The operator console 114 is operably connected with the image capturing unit 112 and configured for control of the image capturing unit 112 to administer a scan. The operator console 114 includes an input device(s), such as a keyboard, touchscreen, mouse, and/or joystick, configured to allow an operator to control a scanning device and/or enter information, as well as an output device, such as a display screen, to provide information to the operator regarding, for example, a scan under process, preliminary results of a scan, or a reconstructed image subsequently provided by the processing center 130. As many imaging techniques must be performed under carefully controlled circumstances to minimize risk, for example, of overdosing or overexposing a patient to radiation, the operator console 114 may be configured to allow an operator to administer, control, and/or oversee a scan. Conventionally known imaging systems typically use a large amount of processing capability at either or both of a console or an associated workstation for reconstructing an image. Embodiments allow for an operator console of reduced expense and maintenance by removing the image reconstruction and attendant processing requirements from the site of the medical scanning process.

In the illustrated embodiment, the on-site processing module 116 is operably connected with the operator console 114, the data storage module 118, and the image capturing unit 112. The processing module 116 is configured to analyze data obtained during a scan (provided to the processing module 116 by the image capturing unit 112 and/or the data storage module 118), and to verify that the image information acquired during the scan is acceptable for reconstruction of an image. The processing module 116 in embodiments performs a preliminary reconstruction at a generally low level of detail to confirm that the data acquired is of an acceptable quality for subsequent use (e.g. includes the region of interest). Thus, the processing module 116 in some embodiments has considerably lower processing requirements than that required for a full reconstruction, and will not have associated therewith the same capital expense, maintenance, regulatory validation, or updating challenges as other on-site image reconstruction systems. For example, if a patient moves an amount sufficient enough to prevent acceptable reconstruction of an image, the processing module 116 may detect the movement above a given threshold or the quality of data below a given threshold of quality and inform the operator via the operator console 114 of any issues. In embodiments, the processing module 114 may also provide the operator with suggestions for possible resolution of any issues, such as increasing a time of scan.

The data storage module 118 is operably connected to all or some of the other components of the medical scanning system 110 described herein and is configured to store data for use by the other modules and/or users of the medical scanning system and/or administrators of a facility associated with the medical scanning system. For example, the data storage module 118 may store data acquired by the image capturing unit 112, or information entered via the operator console 114. The data storage module 118 may comprise and/or be associated with a picture archiving and communication system (PACS). A PACS system, for example, provides access to viewable images and associated data. Because the information in a PACS system may include patient-specific information, PACS systems include appropriate security for safeguarding such information.

The processing center 130 includes an input module 140, an image reconstruction module 150, an output module 160, a data storage module 170, and a tracking module 180. The processing center 130 may comprise a single processor, or may comprise a plurality of processors performing different processing tasks and/or sharing responsibility for processing tasks, with the plurality of processors located at a single location, or, as another example, with one or more of the plurality of processors located remotely from each other. For example, the processing center 130 may comprise a server farm. For example, the processing center 130, in embodiments, includes a server that is administered by a user. In such embodiments, the user may retain ownership of the server and the software, with software purchased on a right to use basis. The input module 140 is configured to receive image acquisition information as well as to determine and/or receive instruction regarding processing of the image acquisition information. The image acquisition information is then sent to the image reconstruction module 150, where an image is reconstructed using the image acquisition information. The output module 160 provides the reconstructed image to a viewer, for example, by transmitting the reconstructed image to a viewer, or, as another example, allowing a viewer access to the reconstructed image. The tracking module 180 tracks the reconstruction of the image and associated activity, for example, for billing purposes, or, as another example, for benchmarking purposes.

The input module 140 is configured to receive image acquisition information, or imaging information, that has been acquired by the medical scanning system 110. The input module 140 is communicatively coupled to the medical scanning system 110 so that the input module 140 may receive the imaging information. The input module 140 may include a data exchange connection. In some embodiments the input module 140 may utilize known internet protocols, while in other embodiments, the input module 140 may utilize other exchange protocols. For example, the input module 140 may be communicatively coupled with the medical scanning system 110 by a high speed internet connection. In embodiments, the input module 140 is configured to receive image acquisition data provided by the medical scanning system 110, determine a type or types of processing to be performed by the image reconstruction module 150, confirm that the medical scanning system 110 and/or a user or entity associated therewith has permission to have an image reconstructed, and, if the user or entity has permission, provide the image acquisition data to the image reconstruction module 150 for reconstruction of the image.

In the illustrated embodiment, the input module includes a user interface module 142, a data reception module 144, and a processor access module 146. The user interface module 142 is configured to allow a user (such as practitioner operating the medical scanning system 110) to interact with the processing center 130, for example, to identify and/or confirm a reconstruction processing type to be utilized. In the illustrated embodiment, the data reception module 144 receives the image acquisition data from the medical system, performs any associated analysis, and forwards the information to the image reconstruction module 150. The processor access module 146 determines whether a request for permission is authorized, or if a requestor has permission for a requested reconstruction.

The user interface module 142 is configured to allow a user (such as a practitioner operating the medical scanning system 110) to interact (for example, in conjunction or cooperation with a display at a user site communicatively coupled with the user interface module 142) with the processing center 130, for example, to identify and/or confirm a reconstruction processing type to be utilized. For example, at or around the time of transmitting the image acquisition data to the processing center 130, a user may enter instructions regarding the type of processing to be performed. Such an example may include not only an identification of a type of imaging information to be reconstructed (e.g., MRI, CT, PET), but also may include a specific type of software (e.g. identifying features required, such as correction of motion artifacts) or intensity level of processing to be performed (e.g. less intensive processing where additional detail or resolution may not be required, or more intensive processing where additional detail or resolution may be required; less intensive processing where additional data is provided or more intensive processing where less data is provided). In embodiments, a user may initially specify a type of imaging information or scanning type without specifying a type or level of processing. In other embodiments, a user may not initially specify type of imaging information or a level of processing, for example, waiting for a prompt to select processing type, or, as another example, the processing center may autonomously select a processing technique based on the image acquisition information provided.

In embodiments, the user interface module 142 may provide a menu of selections from which a user may select a desired processing type and/or level. Such a selection, for example, may be communicated to the medical scanning system 110 and displayed on a screen of the operator console 114. Further, in embodiments, the user interface module 142 may provide a screen that is tailored to the individual user and/or an organization with which the user is associated. For example, if a given hospital has subscribed or otherwise has access to a subset of processing options, the user interface module 142 may provide a screen to the user highlighting the subset of processing options available at no charge, and optionally also providing a list of other available processing options. The list of other available options may be accompanied by an identification of an associated charge that must be paid before such other available options may be utilized. Further still, the user interface module 142 may offer additional processing options to a user. For example, the user interface module 142 may identify a new type of processing option, provide a description of the new type of processing option, and offer the user a free trial of the new type of processing option. In embodiments, similar features or functionality may be provided for user interaction with the remote viewing system 190.

In embodiments, the user interface module 142, independently or in conjunction with the data reception module 144, for example, may perform an analysis of the provided image acquisition data and provide one or more recommendations for processing based on the provided image acquisition data, for example based on a quantity or a quality of the image acquisition data. In embodiments, the user interface module 142 may, for example, provide one or more suggested processing techniques based at least in part on a user's subscription or access level, a user's past preferences, a user's recently used processing techniques for comparable or similar data, processing techniques used by other users for similar or comparable data, or a combination of two or more of the above bases. In embodiments, the user interface module 142, in addition to providing processing options covered by a user's subscription or access level, may also suggest appropriate processing types not covered by a user's subscription or access level that appear appropriate based on an initial analysis of the provided image acquisition data. In embodiments, a user may have a pre-defined default processing selection, and the user interface module 142 may provide alternatives to the default processing selection. In some embodiments, the user interface module 142 receives a processing selection, while in other embodiments the user interface module 142 suggests a processing selection subject to a user's approval, while in still other embodiments the user interface module 142 autonomously selects a processing selection.

For example, a processing center may offer two levels of processing for image acquired during a PET scan, named for the sake of simplicity in the present example as "PET1" and "PET2." In this example, "PET1" is a less intensive processing that requires a first amount of data, and "PET2" is a more sophisticated processing that requires a second amount of data that is less than the first amount to provide an acceptable reconstructed image. If a user provides an amount of data that is sufficient for processing with "PET2" but not with "PET1" (or is questionable with respect to "PET1"), the user interface module 142 may prompt the user that use of "PET1" (which requires more data) may not provide a desired image quality, and suggest use of "PET2" (which requires less data) instead. If "PET2" is not already available to the user, the user interface module 142 may provide pricing or other information regarding obtaining access to use of "PET2" for processing. Further, the user interface module 142 may provide the user with an option to agree to a payment for use of "PET2," if required, or, in embodiments, may offer a user a free trial of "PET2" on one or more occasions, for example up to a predetermined maximum number of free trials per user or customer.

As yet another example, if the amount of data provided is sufficient for satisfactory use of "PET1," the user interface module 142 may recommend use of "PET1" for the particular scan being processed, but also provide a prompt about the availability of "PET2" and inform the user that use of "PET2" for future processing will require a smaller amount of data (and a corresponding lower amount of exposure to a patient during a scanning procedure). Thus, the user interface module 142 may recommend an appropriate processing technique for a current scan and/or provide information about additional processing techniques. The above example is meant by way of illustration only, as numerous other interactions or prompts with a user regarding selection of processing type or level are contemplated by embodiments of the present inventive subject matter.

The data reception module 144 receives the image acquisition data from the medical scanning system 110. Data transmission between various aspects of the system 100 may contain information that implicates privacy concerns. As appropriate, the components of the system 100 utilize appropriate protocols and procedures to maintain privacy, such as compliance with the Health Insurance Portability and Accountability Act (HIPAA) and/or other appropriate standards.

In the illustrated embodiment, the data reception module 144, for example, may perform an initial analysis of the data to determine the type, quality, and/or quantity of the data. For example, as also discussed above, the data reception module 144 may, in conjunction with the user interface module 142, identify an appropriate processing technique or techniques based on the received data, and provide a user with information regarding the identified processing techniques.

In embodiments, the data reception module 144 may receive the image acquisition data from the medical scanning system 110 in a standardized format. For example, the medical scanning system 110 may send information to the processing center 130 according a communication protocol such as Digital Imaging and Communications in Medicine (DICOM). Use of data sent under a standard protocol, such as DICOM, can help ensure a minimum standard for the data sent, as well as provide compatibility across different vendors. For example, conventional scanning systems are typically limited in functionality, in that only software from the provider of the equipment itself is typically compatible with and usable with a particular piece of equipment. Various embodiments, however, allow the use of, for example, software from a first vendor to be used with imaging or scanning data acquired with a scanning device of a different, second vendor. In other embodiments, data sent to the processing center 130 may be sent in a raw or unprocessed form, or, for example, in a list mode that includes time stamp data.

The processor access module 146 determines whether a request for permission is authorized, or if a requestor has permission for a requested reconstruction. For example, the processor access module 146 may receive, from the user interface module 142 and/or the data reception module 144 and/or the medical scanning system 110, information that identifies a user or facility associated with a user, as well as a processing activity requested. The processor access module 146 then determines whether the particular user has access or permission to utilize the particular processing activity requested. For example, the processor access module 146 may access a database including information regarding users and the processing techniques to which each user has pre-approval or for which each user is covered by a subscription. In embodiments, such a database may be stored in a data storage unit that is part of, assigned or dedicated to, or otherwise associated with the processor access module 146. In alternate embodiments, such a database may be maintained in a separate location that may be remote or may not be remote from the processor access module 146.

For example, if the requested processing activity is authorized for the user making the request, the processor access module 146 may direct the user interface module 142 to provide a prompt confirming to the user that the requested processing is available, and also direct the image reconstruction module 150 to begin the image reconstruction using the selected processing technique. Or, if the requested processing activity is not authorized for the user making the request, the processor access module 146 may direct the user interface module 142 to provide a prompt informing the user that the requested processing is not available, and avoid directing the image reconstruction module 150 to begin processing until access or permission has been granted.

The prompt to the user informing the user that the requested processing is not available may include information on alternative processing techniques that are already available to the particular user, and/or inform the user of any steps, such as additional subscriptions and/or payments that may be required to utilize the selected processing techniques. For example, the user interface module 142 may provide the user with information regarding pricing for a one time usage of the requested processing technique, and/or information regarding one or more subscription packages that would include the requested processing technique on an ongoing basis. For example, access may be granted to all or a portion of available processing techniques on a subscription basis, on a pay-per-use basis, or a combination thereof. The user interface module 142, in embodiments, may provide a user information regarding how much processing has been utilized and/or how much processing time remains for a given a billing cycle. Further, in embodiments, the user interface module may offer a new service to a user and/or recognize a promotion code After image acquisition or scanning information has been received, an appropriate processing technique determined, and authority granted to a particular user, the image information along with identification of processing is provided to the image reconstruction module 150 by the input module 140. The image reconstruction module 150 is configured to reconstruct an image using the image acquisition data provided by the medical scanning system 110 and the selected processing technique.

For example, the data reception module 140 may forward the image acquisition data to the image reconstruction module 150. The processing access module 146, after confirming the availability of a selected processing technique to a user, may inform the image reconstruction module 150 of the selected processing technique, and also direct the image reconstruction module 150 to reconstruct the image using the selected processing technique. In the illustrated embodiment, the image reconstruction module 150 includes a software library module 152, an update module 154, and a processing module 156.

The software library module 152 provides access to one or more software programs configured to perform a given image reconstruction processing technique or techniques. In embodiments, the software library module 152 includes a variety of software options covering different types, levels, and/or functionalities of processing options, thereby allowing for wide range of software to be used (see also FIG. 2 and related discussion below). The software library module 152 may be operably linked with one or more aspects of the input module 140, such as the user interface module 142 and/or the data reception module 144, so that one or more aspects of the input module 140 have access to current lists of software potentially available for image reconstruction processing for one or more imaging modalities, and select from such a current list when providing any recommendations or suggestions to a user. The software library module 152 helps provide a wide range of software to be available to a greater number of users than previously allowed in known on-site processing systems. For example, a type of processing software that is used only rarely or occasionally may be cost prohibitive for installation and/or operation on-site at a scanning site. However, such a processing software type may be populated in the software library module 152 of the processing center 130 where the software can be accessed by a large number of users, for example, for one-time, occasional, limited, and/or trial usage at considerably lower expense than for on-site usage.

Figure 2:
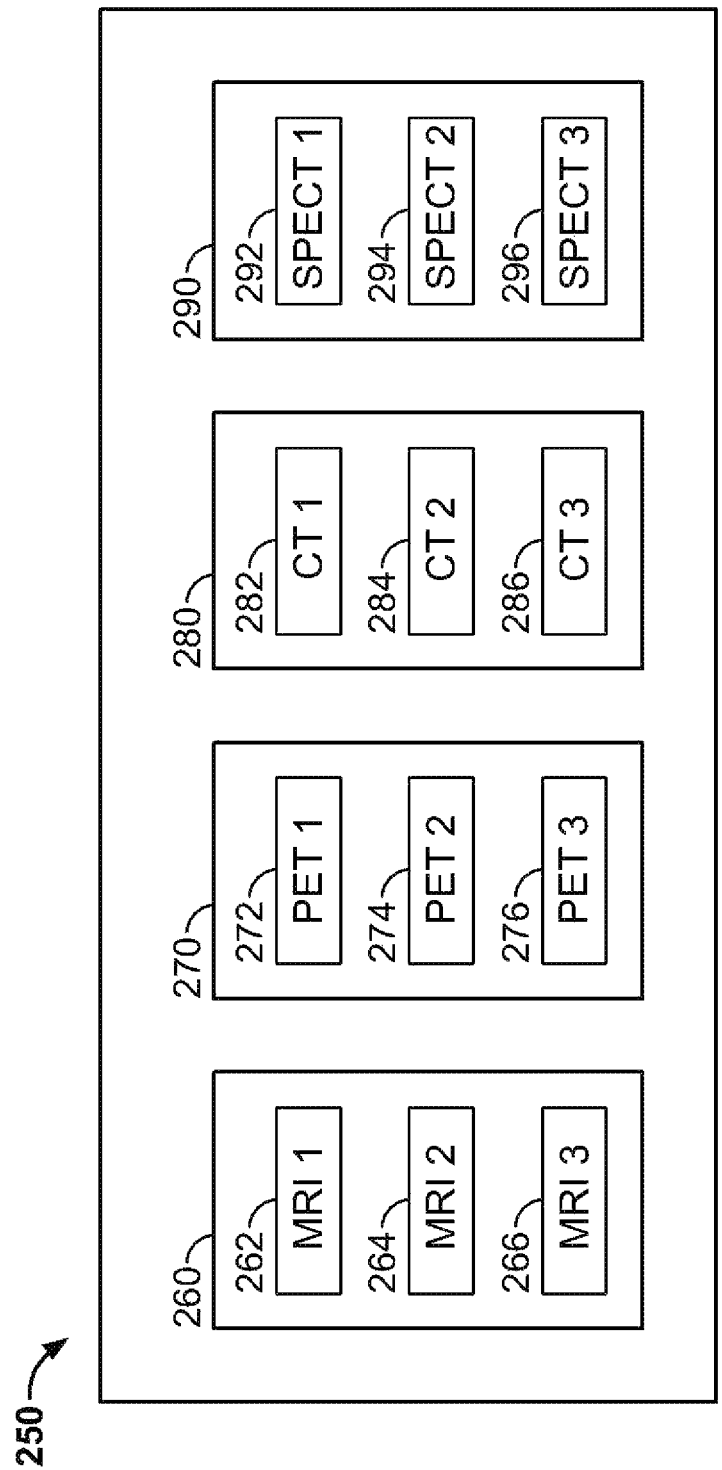
FIG. 2 is a block diagram of a software library module for an imaging system in accordance with various embodiments.

For example, FIG. 2 illustrates a schematic view of a software library module 250. The software library module 250 includes an MRI sub-library 260, a PET sub-library 270, a CT sub-library 280, and a SPECT sub-library 290. Each sub-library of the embodiment depicted in FIG. 2 includes three different types of software representing three different processing techniques for each type of scanning system (e.g. MRI, PET, CT, SPECT). The arrangement depicted in FIG. 2 is for illustrative purposes, and a wide variety of other arrangements for library modules are contemplated for alternative embodiments. For example, in certain alternate embodiments, a processing center and/or a software library module may be dedicated to fewer or more types of scanning systems, and may include fewer or more types of processing techniques per scanning system type. Additionally or alternatively, a software module library may be customized for and dedicated to a given user or group or groups of users.

The MRI sub-library 260 includes a first MRI processing software program 262, a second MRI processing software program 264, and a third MRI processing software program 266. Each of the processing software programs provides a different type or level of processing. For example, in embodiments, the first MRI processing software program 262 provides a generally less intensive processing technique that has fewer features, lower image quality, and/or higher data requirements, but uses less processor time and/or is less expensive. The third MRI processing software program 266 provides a generally more intensive processing technique that has an increased number of features, higher image quality, and/or lower data requirements, but uses more processor time and/or is more expensive. The second MRI processing software program 264 may be generally intermediate in expense and processing sophistication between the first MRI processing software program 262 and the third MRI processing software program 266.

Thus, in contrast to systems that may provide only a single type of software, a user has a selection of a plurality of processing techniques that can be tailored and varied based on individual scans, including the quality and/or quantity of data acquired by a scan, and/or the quality of the desired image to be reconstructed. Further, the user does not have to pay the initial outlay for installation of such varied functionalities in the field, nor does the user have to pay the ongoing outlay for maintenance and updating. Instead, the user may be provided a wide variety of processing techniques on a subscription basis, and/or access to processing techniques on a pay-per-use basis. For example, a user may use one type of processing technique a majority of the time, and a more expensive processing technique only occasionally. Instead of having to choose, on the one hand, between undertaking a large investment and associated maintenance responsibilities for a rarely used technique, and, on the other hand, forgoing a technique entirely, the user may, in embodiments, be provided with convenient and relatively inexpensive access to a technique that is used only occasionally.

Thus, in embodiments, the processing module may reconstruct an image using a processing technique selected from a plurality of processing techniques available to the processing module. In embodiments, the selection may be made autonomously by the processing module, for example, based upon scanning data received. The plurality of techniques may include a plurality of sub-groups of techniques relating to a corresponding plurality of imaging modalities (e.g. SPECT, PET, CT, MRI).

In embodiments, programs may be used additionally to each other. For example, a first program may provide for a basic level of processing for image reconstruction, and other programs may be available to combine with the first program to add a feature or functionality to the first program. For example, a first program may provide for a basic level of processing, but a customer may choose to use in conjunction with the first program a second program that includes added or improved functionality, for example, to address movement artifacts in a scan. The user may choose to use such an added functionality based on observation during administration of a scan, or based on a suggestion or prompt from, for example, the user interface module 142. For example, a user may notice excessive movement from a patient during a scan, and thus select the added functionality when requesting the image reconstruction. As another example, the input module 140 may perform an initial analysis of scanning data provided, and detect a larger than desirable amount of motion artifacts in the data. The user interface module 142 may then inform the user of the motion and offer the additional software with the added functionality for use in processing the scan.

In the illustrated embodiment, the various sub-libraries are arranged generally similarly. For example, the PET sub-library 270 includes a first PET processing software program 272, a second PET processing software program 274, and a third PET processing software program 276. The CT sub-library 280 includes a first CT processing software program 282, a second CT processing software program 284, and a third CT processing software program 286. The SPECT sub-library 290 includes a first SPECT processing software program 292, a second SPECT processing software program 294, and a third SPECT processing software program 296. As discussed above, each of the processing software programs provides a different type or level of processing. In alternate embodiments, sub-libraries may be arranged differently from each other, and a fewer or greater amount of sub-libraries may be employed. Further, in embodiments, a given software or processing technique may be configured to be used with more than one modality of scanning system.

Returning to FIG. 1, the updating module 154 is configured to update the software library module 152. Thus, the software library module 152 may be maintained so that the software available is up-to-date and, for example, state of the art, without requiring the expense and inconvenience of multiple on-site installations and associated multiple regulatory validations. Instead, in embodiments, all updating, and related regulatory validation, may be performed at or for only the processing center 130. In embodiments, the updating module 154 autonomously updates the software library module 152. For example, an update (either a modification to an existing image reconstruction software program or a new program to be added) may be downloaded to the updating module 154 after the software is finalized and validated for regulatory purposes. Then, the updating module 154 will update the software library module at a convenient time, such as a time when requests are not being received, or a predetermined time when requests are not commonly received. In other embodiments, the software library module 152 may be updated by an operator. Embodiments thus provide for seamless, timely updates to image reconstruction software while greatly reducing the time, expense, and inconvenience of updates experienced by certain presently known scanning systems.

The processing module 156 accesses software from the software library module 152 to reconstruct an image using a selected technique. For example, the input module 130 may pass along image acquisition data (either in the form obtained from the medical scanning system 110 or in a modified form) to the image reconstruction module 150, along with an instruction describing the processing technique selected. The processing module 156 then uses the appropriate software from the software library module 152 based on the processing technique selected, to reconstruct an image using the scanning data provided by the medical scanning system 110.

The processing module 156, either independently or in conjunction with other aspects of the processing center 130, may suggest software before, after, or during processing based on information available to the processing module 156. For example, if it is determined during the image reconstruction process that there is an issue with the data being used with respect to the technique being used (for example, based on a quality or quantity of data being used), the processing module 156 may identify the issue and/or provide a proposed solution (for example, providing additional data and/or using a different processing technique) in conjunction with the user interface module 142 of the input module 140 and/or the user interface module 164 of the output module 160.

In the illustrated embodiment, both the software library module 152 and the processing module 156 are provided in one centralized location. In other embodiments, the processing module 156 and the software library module 152 may be located remotely from each other. In still other embodiments, the processing may be centralized while the software is not centralized, while in others the software may be centralized while the processing is not (e.g. up-to-date software is provided by a centralized software center, while processing is still performed locally relative to the medical scanning system 110).

After the image is reconstructed, the reconstructed image is transmitted to the output module 160. The output module 160 is configured to provide access to the image reconstructed at the processing center to at least one of the medical scanning system 110 or a requestor located remotely from the processing center.

For example, the output module 160 may transmit a reconstructed image to the medical scanning system 110 or to another location for viewing and/or further manipulation or processing of the reconstructed image. Alternatively or additionally, the output module 160 may provide access to a user to view the reconstructed image from the processing center 130. In the illustrated embodiment, the output module includes a transmission module 162, a user interface module 164, and an image access module 166.

The transmission module 162 is configured to transmit or provide image reconstruction data or provide access to image reconstruction data, such as one or more reconstructed images, to a requestor, for example, a medical scanning system that previously sent data used to reconstruct a particular image, or, as another example, a workstation being used by a practitioner that performed the scan or otherwise associated with a customer from which data was received to reconstruct the requested image. The transmission module 162 may be configured to automatically transmit the reconstructed image, or may transmit the reconstructed image responsive to a request or other prompt, for example confirmation of a password or other user identification confirming that the party receiving the requested image has authorization to receive the image, or, as another example, the transmission module 162 may be configured to provide access to the reconstructed image responsive to a request or other prompt, for example confirmation of a password or other user identification confirming that the party receiving the requested image has authorization to access the reconstructed image. The transmission module 162 may include a data exchange connection. In some embodiments the transmission module 162 may utilize known internet protocols, while in other embodiments, the transmission module 162 may utilize other exchange protocols. The transmission module 162 may include, for example, a high-speed internet connection for transmitting images.

The user interface module 164 of the output module 160 is configured to allow or facilitate interaction between a user or requestor of an image and the processing center 130 (for example, in conjunction or cooperation with a display at a user site communicatively coupled with the user interface module 164). For example, the user interface module 164 of the output module may be generally similar in certain respects to the user interface module 142 of the input module 140. In embodiments, the user interface module 164 identifies potential issues with a reconstructed image, and prompts a user with respect to potential resolutions to any such issues.

For example, motion artifacts may be detected or a substantial amount of motion may otherwise be identified as causing an image quality issue. The user interface module 164 may provide interaction with a user to address such an image quality issue. For example, the user interface module 164 may issue a prompt indicating the quality issue, and suggest processing the data with an alternate processing technique that will better address the motion in the image acquisition data to produce a higher quality reconstructed image. Such a prompt may be accompanied by information regarding whether the particular user already has permission or authorization to use the proposed different processing technique, or information regarding what steps must be taken to obtain access to the proposed processing technique, such as providing information regarding pricing (e.g. pricing information describing a one-time or other limited use charge, or pricing information regarding one or more subscription packages including the proposed technique and the difference between such packages and the current subscription pricing of the user.) As another example, if there appears to be an issue with image quality based on a lack of sufficient imaging data for a previously attempted processing technique, the user may be provided with information regarding a more appropriate processing technique for the amount of data available.

In embodiments, the user interface 164 of the output module 160 may provide a "sneak preview" of the image to help a user determine, for example, if additional processing is required or if the reconstructed image will be satisfactory. For example, when the processing center 130 has determined that motion artifacts may present a substantial quality issue, the user may be provided with all or a portion of an image, along with a prompt indicating that image quality may have been compromised by a quality issue, such as motion artifacts. If the image quality is indeed not acceptable to the user, the user may then, for example, be provided with an alternative or additional processing technique to address the image quality. In embodiments, the user interface 164 may provide sample images demonstrating what improvements in image quality may be accomplished using different processing techniques.

The image access module 166 is configured to allow an authorized requestor to view one or more images available from the processing center 130. For example, a user may enter a password or otherwise provide authorization information. If the authorization information is sufficient, the user may then be provided access to view images from the processing center 130 associated with the authorization identification provided by the user. For example, a user that provided authorization information associated with a particular customer, such as a hospital, may be granted access to view images reconstructed from scanning data provided by users associated with the particular customer.

The image access module 166, in embodiments, also provides access to manuals or other training materials associated with, for example, any processing techniques used to reconstruct an image being viewed. As another example, the image access module 166 may provide access to training materials for any processing techniques identified or recommended by the processing center 130 for a given viewer or user, for example, based on a benchmarking analysis. For example, if the provided image acquisition data and/or selection of processing technique differs substantially from industry standards or common practices of other users, for a given type of scan, the user may be informed of such a difference. Further still, the image access module 166 may provide training materials in response to a request. Additionally or alternatively, access to training materials, for example as described above, may also be provided via the user interface 164. In embodiments, the image access module 166 may cooperate with or be integrated with the processing access module 146.

The data storage module 170 is operably connected to one or more other modules, portions, or aspects of the processing center 130. The processing center 130 may include more than one data storage, including, for example, one or more data storages dedicated to one or more particular modules. Data, for example, regarding reconstructed images may be stored for subsequent access by a remote viewer. Alternatively or additionally, the data storage module 170 may store data for use by a benchmarking or billing module. Also, the data storage module 170 may work in conjunction with the software library module 152, for example providing storage for new updates, or archiving previous software versions. In embodiments, the data storage module 170 stores a subscription data base or other access list for the processing access module 146 and/or the image access module 166.

The tracking module 180 is configured to collect information recording, organizing, summarizing and/or analyzing image reconstructions and related processing information. The information may be specific to a particular customer (as one example, a summary of characteristics of all scans of one or more types of procedures by a particular customer, or, as another example, billing or subscription information for a particular customer). Alternatively or additionally, the information may be collected or analyzed across all or a group of customers. For example, characteristics of data provided and/or processing techniques used for a particular type of scan (e.g. a scan of a particular aspect of patients) may be recorded and tracked by the tracking module 180. In the illustrated embodiment, the tracking module 180 includes a billing module 182 and a benchmarking module 184.

The billing module 182, for example, collects info illation regarding the number and type of processing used by a given customer, and identifies any charges that may be need to be made in addition to any subscriptions already associated with that given customer. Further, in embodiments, the billing module 182 analyzes processing activity by customers with respect to the customers' respective subscriptions, and identifies if a subscription level of a customer does not match well with the processing being requested on a periodic basis by the customer.

The benchmarking module 184, for example, may, in conjunction with either or both user interfaces 142, 164 provide suggestions to a requestor of a scan. For example, the benchmarking module 184 may track characteristics, such as amount of data provided, length of scan performed, and/or type of processing technique employed, for each image reconstruction requested. Thus, the benchmarking module 184 may have recorded, for example, an average amount of data for a given scanning procedure for imaging a given aspect of a patient. This average amount of data may then be compared to an amount of data provided by a requestor. The processing center 130 may then inform the requestor of how the amount of data the requestor obtained compares to the average amount of data provided by other requestors reconstructing a similar image. This allows to requestors to identify any potential procedures that may benefit from adjustment. For example, if, for a given type of scanning procedure of a given aspect of a patient, the average time of scan is substantially smaller than the time of scan by a requestor, the requestor may consider performing shorter scans in the future.

As another example, the benchmarking module 184 may track the processing techniques employed most frequently for a given type of scanning procedure. Such tracking may then be used in developing recommendations to a requestor. Benchmarking may be performed for one or more types scans requested by a given customer, for one or more types of scans by all customers, and/or for one or more types of scans performed by a group or groups of customers.

The benchmarking and/or billing information may be provided, for example, to the output module 160 for automatic transmission to a customer. Additionally or alternatively, the benchmarking and/or billing information may be available to a requestor via the image access module 166. Yet further still, benchmarking and/or billing information may be provided via the user interface 142 of the input module 140 and/or the user interface 164 of the output module 160, either in connection with the processing of a scan or independent of the processing of a scan.

The remote viewing system 190 is configured to allow a user or requestor remotely located from the processing center 130 to view a reconstructed image. In the illustrated embodiment, the remote viewing system 190 includes a computer 192 (including input device(s) such as a keyboard, mouse, and/or touch screen, a display such as a screen, a processor, etc.) and a data storage module 194. In embodiments, the computer 192 may be a personal computer, while in other embodiments, the computer 192 may be a more powerful workstation configured as a desktop or a laptop. In some embodiments, the remote viewing system 190 may be remote from the medical scanning system 110, while in other embodiments the remote viewing system 190 may not be remote for the medical scanning system 110. The structure and/or functionality of the remote viewing system 190 may also be provided as part of the remote medical scanning system 110 so that an operator of the remote medical scanning system may view images reconstructed by the processing center 130.

The computer 192, for example, receives a reconstructed image from the processing center, and is configured to allow an operator of the computer 192 to view the reconstructed image. The computer 192, in embodiments, is also configured to allow for post-processing manipulation of the reconstructed image, for example to allow a user to more easily study a given portion of the reconstructed image.

The data storage module 194 may be generally similar in respects to the data storage module 118 of the medical scanning system 110. For example, the data storage module 194 may store data regarding the reconstructed image acquired from the processing center 130. The data storage module 194 may also store PACS data. Because the information in a PACS system may include patient-specific information, PACS systems include appropriate security for safeguarding such information.

Figure 3:
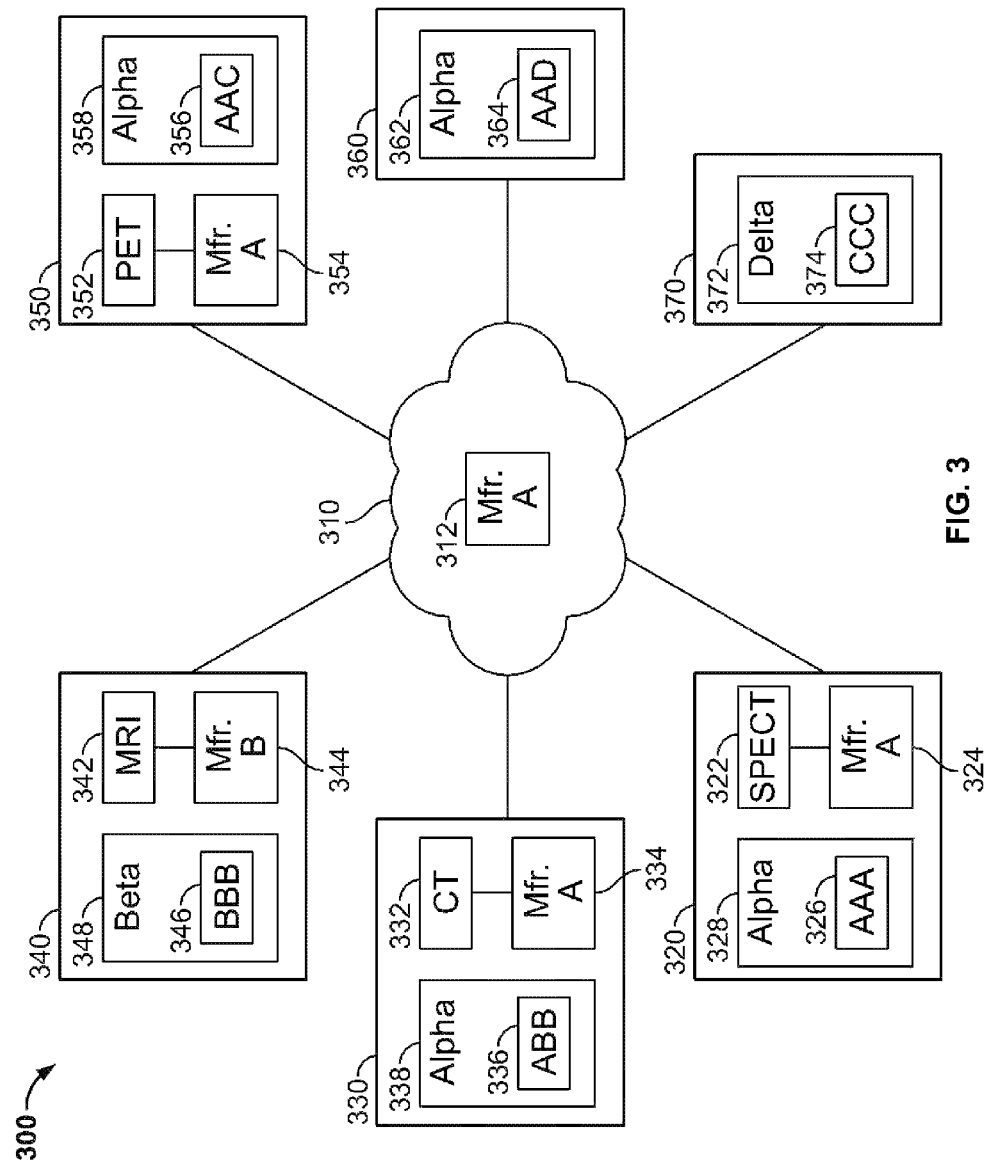
FIG. 3 is a schematic view of an imaging system in accordance with various embodiments.

FIG. 3 provides an example of the use of different types of devices that are administered by different parties and/or provided by different parties. For example, data may be provided to a central processing station in a standardized format so that a device operated by a first party and provided by a second party, may use software of a third party. The example of FIG. 3 is intended to be illustrative, not exhaustive, and a wide variety of other arrangements may be employed by alternate embodiments.

FIG. 3 provides a schematic depiction of a distributed image reconstruction system 300 formed in accordance with embodiments. The distributed image reconstruction system 300 includes a processing center 310, a SPECT scanning system 320, a CT scanning system 330, a MRI scanning system 340, a PET scanning system 350, a first remote workstation 360, and a second remote workstation 370. In the illustrated embodiment, the processing center is configured to reconstruct images from a variety of different types of scanning systems (e.g. SPECT, CT, MRI). In other embodiments, a plurality of processing centers may be employed, with the processing centers providing similarly widespread functionality as depicted in FIG. 3, or, in other embodiments, a given processing center may be dedicated to one particular type of scanning system (e.g. a first processing center for processing SPECT data, a second processing center for processing CT data, a third processing center for processing MRI data, etc.) In still further embodiments, a given processing center may be dedicated to a given geographical area, or, as another example, to a particular customer or user or particular groups of customers or users. The examples discussed herein are given as examples for illustrative purposes only, as other numbers or arrangements of processing centers are contemplated by the present inventive subject matter.

The processing center 310, for example, may be configured generally similar to the processing center 130 discussed above in connection with FIGS. 1 and 2. The processing center 310 is communicatively coupled with the SPECT scanning system 320, the CT scanning system 330, the MRI scanning System 340, the PET scanning system 350, the first remote workstation 360, and the second remote workstation 370 via, for example, the internet utilizing a cloud arrangement. In the illustrated embodiment, the processing center 310 is administered by an administrator 312. In the illustrated embodiment, the administrator 312 is identified as "Manufacturer A" and is a manufacturer and a vendor of scanning devices. In the illustrated embodiment, the processing center 310 utilizes software prepared by the vendor "Manufacturer A." In alternate embodiments, the administrator 312 of the processing center 310 may be, for example, a developer of image reconstruction software but not scanning equipment, or, as another example, neither a developer of image reconstruction software nor a developer of scanning equipment. As another example, the processing center 310 may utilize image reconstruction software provided by a plurality of software developers. Such software may be stored and updated at the processing center 310, and/or may be stored and administered remotely from the processing center 310. For example, one or more remote processing centers may access software from one or more remote software libraries. Each of the various systems and/or workstations accessing the processing center may be granted access to the processing center 310 via a subscription arrangement or on a pay-per-use basis.

The SPECT scanning system 320 includes a SPECT scanner 322 manufactured or designed by a vendor 324 and administered by a user 326 of a customer 328. For example, in the illustrated embodiment, the vendor 324 may be a first vendor referred to herein as "Manufacturer A" (e.g. the same party that administers the processing center 310 in the illustrated embodiment). The customer 328 may be a hospital and the user 326 an employee of the hospital administering a scan using the SPECT scanner 322. In the illustrated embodiment, the user 326 is identified as "AAA," a practitioner associated with a hospital "Alpha." The customer 328 administers a scan to a patient to obtain image acquisition data, which is forwarded to the processing center 310, where the image acquisition data is used to form a reconstructed image. The reconstructed image may subsequently be accessed by the user "AAA" and/or another user associated with the hospital "Alpha." For example, a unique password or identification code may be available to authorized user associated with hospital "Alpha" who may then obtain the reconstructed image from the processing center 310 using the unique password or identification code. As another example, the reconstructed image may be transmitted by the processing center 310 to one or more workstations associated with the hospital "Alpha," where the reconstructed image may be accessed by practitioners associated with the hospital "Alpha."

The CT scanning system 330 includes a CT scanner 332 manufactured or designed by a vendor 334 and administered by a user 336 of a customer 338. For example, in the illustrated embodiment, the vendor 334 may be a first vendor referred to herein as "Manufacturer A" (e.g. the same vendor as the above discussed vendor 324.) The customer 338 may be a hospital and the user 336 an employee of the hospital administering a scan using the CT scanner 332. In the illustrated embodiment, the user 336 is identified as "ABB" a second practitioner associated with a hospital "Alpha" (e.g. the same hospital as the above discussed hospital 328). The customer 338 administers a scan to a patient to obtain image acquisition data, which is forwarded to the processing center 310, where the image acquisition data is used to form a reconstructed image. The reconstructed image may subsequently be accessed by the user "ABB" and/or another user associated with the hospital "Alpha." Thus, as described, a plurality of users using a corresponding plurality of scanning systems may access the processing center 310. As the access may be granted, for example, based on subscription of the hospital "Alpha," individual licenses for each scanning system are not required.

The MRI scanning system 340 includes a MRI scanner 342 manufactured or designed by a vendor 344 and administered by a user 346 of a customer 348. For example, in the illustrated embodiment, the vendor 344 may be a second vendor referred to herein as "Manufacturer B." The customer 348 may be a hospital and the user 346 an employee of the hospital administering a scan using the MRI scanner 342. In the illustrated embodiment, the user 346 is identified as "BBB," a practitioner associated with a hospital "Beta." The customer 348 administers a scan of a patient to obtain image acquisition data, which is forwarded to the processing center 310, where the image acquisition data is used to form a reconstructed image. The reconstructed image may subsequently be accessed by the user "BBB" and/or another user associated with the hospital "Beta." Thus, the processing center 310 may provide processing services using software of a first vendor and scanning data from a system designed or provided by a second scanner of a second vendor. For example, compatibility issues that otherwise may present use of such software from a first vendor and scanning data form a system provided by a second vendor may be addressed by providing data to the processing center 310 in a standardized format. DICOM, also discussed above, provides one example of such a standardized format, though other standardized formats may be used in various embodiments.

The PET scanning system 350 includes a PET scanner 352 manufactured or designed by a vendor 354 and administered by a user 356 of a customer 358. For example, in the illustrated embodiment, the vendor 354 may be a first vendor referred to herein as "Manufacturer A." The customer 358 may be a hospital and the user 356 an employee of the hospital administering a scan using the PET scanner 352. In the illustrated embodiment, the user 356 is identified as "AAC," a practitioner associated with a hospital "Alpha." The customer 358 administers a scan to a patient to obtain image acquisition data, which is forwarded to the processing center 310, where the image acquisition data is used to form a reconstructed image. The reconstructed image may subsequently be accessed by the user "AAC" and/or another user associated with the hospital "Alpha."

The first remote workstation 360 is configured to access one or more reconstructed images from the processing center 310. The first remote workstation 360 is administered by a customer 362, and configured to allow a user 364 associated with customer 362 to view a reconstructed image. For example, access to images reconstructed using data provided by users associated with a particular hospital may be granted to users associated with or identified by that particular hospital. For example, in the illustrated embodiment, the customer 362 is the hospital "Alpha," and the user 364 is a practitioner "AAD" authorized by the hospital "Alpha" to view images. Thus, in the illustrated embodiment, practitioner "AAD" may have access to images reconstructed from scans (or a subset of scans) performed by other practitioners associated with hospital "Alpha," but not granted access to images reconstructed from scans performed by practitioners associated with other hospitals, such as "Beta."

The second remote workstation 370 in the illustrated embodiment is configured to provide limited access to a user 372 associated with organization 374. For example, user 372 may be a user "CCC," and the organization 374 referred to as "Delta" (e.g. an organization separate from "Alpha" and "Beta"). For example, user "CCC" may be granted access to non-patient-specific information, such as benchmarking information, from a cumulative analysis or benchmarking module of the processing center 310.

Such information, may include, for example, information describing the length of scanning and/or quantity of data obtained for a particular type of scan by all users of the processing center. The user 372 may be, for example, an independent researcher, or, as another example, a practitioner preparing to perform a scan of a certain type that is interested in learning how long other practitioners may allot or how much data others obtain for such a scan. In embodiments, the user 372 may be associated with a customer, such as hospital "Alpha" and may obtain cumulative information for just that customer, or may obtain information comparing information for that particular customer with all similar scans. For example, for a particular type of scan of a given aspect of a patient, the user 372 may obtain information regarding average length of scan for that particular procedure by a hospital associated with the user 372, and information regarding average length of scan for that particular procedure across all users. If the two averages are substantially different, the user 372 may then perform further research to see if any adjustments are appropriate in the conduct of such scans by the hospital associated with the user 372. As another example, the second remote workstation 370 and/or user 372 may have access limited to billing or subscription information for a particular hospital or organization associated with the user 372.

Figure 4:
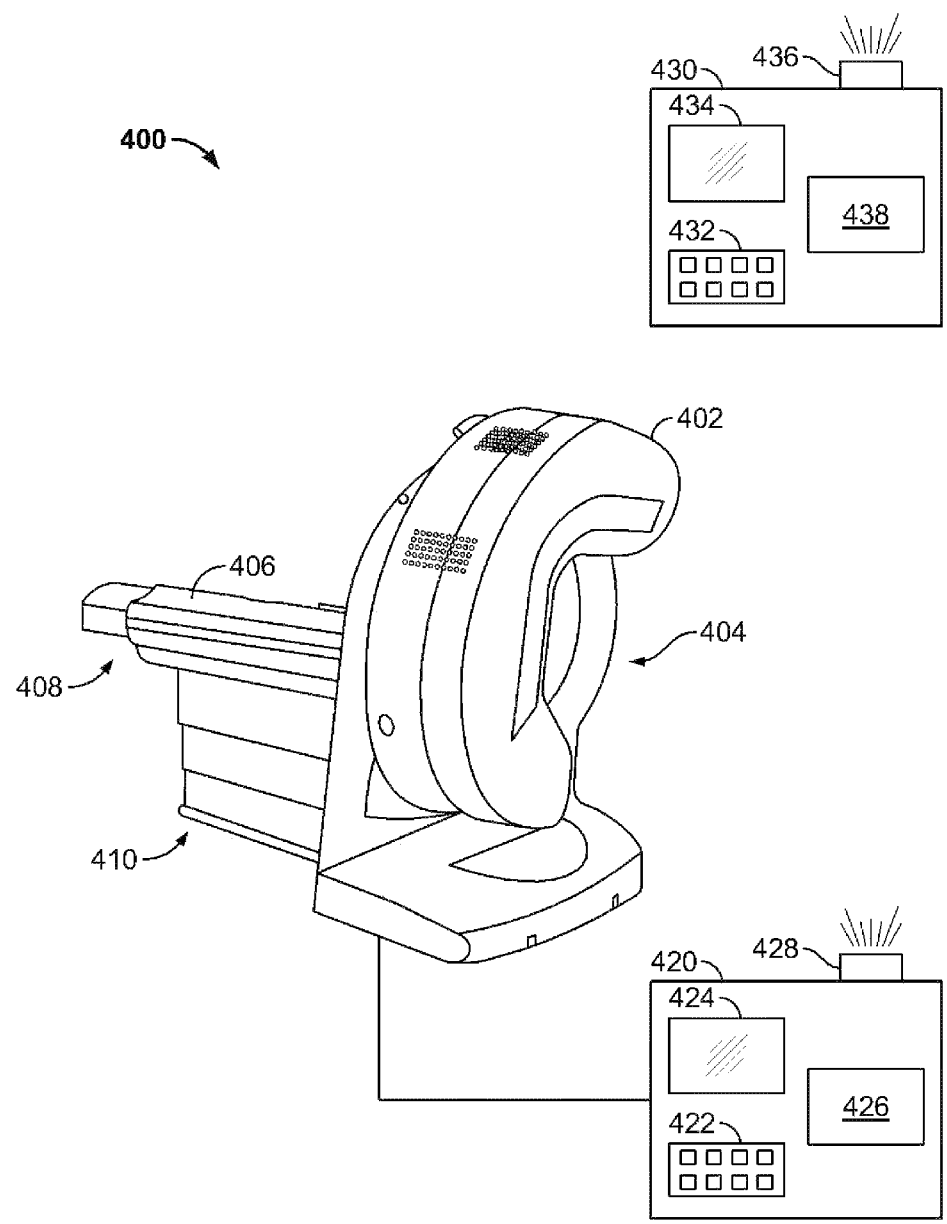
FIG. 4 is an illustration of a medical scanning system formed in accordance with various embodiments.

FIG. 4 illustrates an embodiment of a medical scanning system 400 formed in accordance with various embodiments. The medical scanning system 400 includes scanning equipment as well as an operator console 420, and workstation 430. The operator console 420 is configured to allow an operator to control the operation of a scan and to transmit acquired scanning or imaging data to a processing center (for example, processing center 130 or processing center 310 discussed above), and the workstation 430 is configured to allow a practitioner to view a reconstructed image.

For example, the illustrated medical scanning system 400 may be a NM imaging system, which is shown embodied as a SPECT imaging system. The system 400 includes an integrated gantry 402 having a gantry central bore 404. The gantry 402 is configured to support one or more NM radiation detectors, which may be configured as a pair of detectors that are supported, for example, around 180 degrees of the gantry 402. In such a configuration, the system may include multiple imaging detectors with collimators that are arranged about the object to be imaged, instead of two detectors spaced apart 180 degrees. In embodiments, the NM radiation detectors may be supported around more or less of the gantry 402, for example, around the entire 360 degrees of the gantry 402. Thus, the radiation detectors are arranged around the gantry central bore 404 defining an examination axis.

A patient table 406 may include a bed 408 slidingly coupled to a bed support system 410, which may be coupled directly to a floor or may be coupled to the gantry 402 through a base coupled to the gantry 402. The bed 408 may include a stretcher slidingly coupled to an upper surface of the bed 408. The patient table 406 is configured to facilitate ingress and egress of a patient (not shown) into an examination position that is substantially aligned with the examination axis of the gantry central bore 404. During an imaging scan, the patient table 406 may be controlled to move the bed 408 and/or stretcher axially into and out of (as well as upward and downward within) the gantry central bore 404 to obtain image information for the patient or a region of the patient. It should be noted that the various embodiments may be implemented in connection with imaging systems that include stationary gantries or moving gantries, or other types of imaging systems.

In the illustrated embodiment, the operator console 420 includes an input 422 (keyboard, keypad, mouse, stylus, touchscreen), a display 424, a processing module 426, and a communication module 428. The input 422 provides control over scanning process as well as interaction with a processing center. The display 424 helps monitor scanning process as well as view prompts or other information from a processing center, including processing technique selection, previews of images, or reconstructed images. The processing module 426 in various embodiments is generally reduced in capability (as well as expense) from conventionally known on-site processors, and generally provides substantially a minimum of processing capability to ensure that only valid imaging data is sent and processed, thereby minimizing capital outlay for the operator console 420 and maintenance and updating cost and inconvenience of the operator console 420, while still helping to reduce or prevent expense and inconvenience of transmitting data that is not usable. The communication module 428 includes necessary hardware to communicate with a processing center, for example to transmit image acquisition data to a processing center, to interact with the processing center (e.g. an user interface module of a processing center), to select an appropriate processing technique, and/or to receive reconstructed images from the processing center for use by a practitioner using the operator console. For example, the operator console 420 may be configured to communicate with the processing center via the communication module 428 over a high-speed internet connection.

The workstation 430 may be similar in certain respects to the operator console 420, and includes an input 432, a display 434, and a communication module 436, and a processor 438. The communication module 436, for example, may include a high-speed internet connection configured to receive one or more reconstructed images from a processing center. The processor 438 or the workstation 430 may be utilized, for example, to perform post-processing manipulation of a reconstructed image provided by the processing center. In embodiments, some or all of the functionality and/or components of the workstation 430 may be included in an operator console 420.

Figure 5:
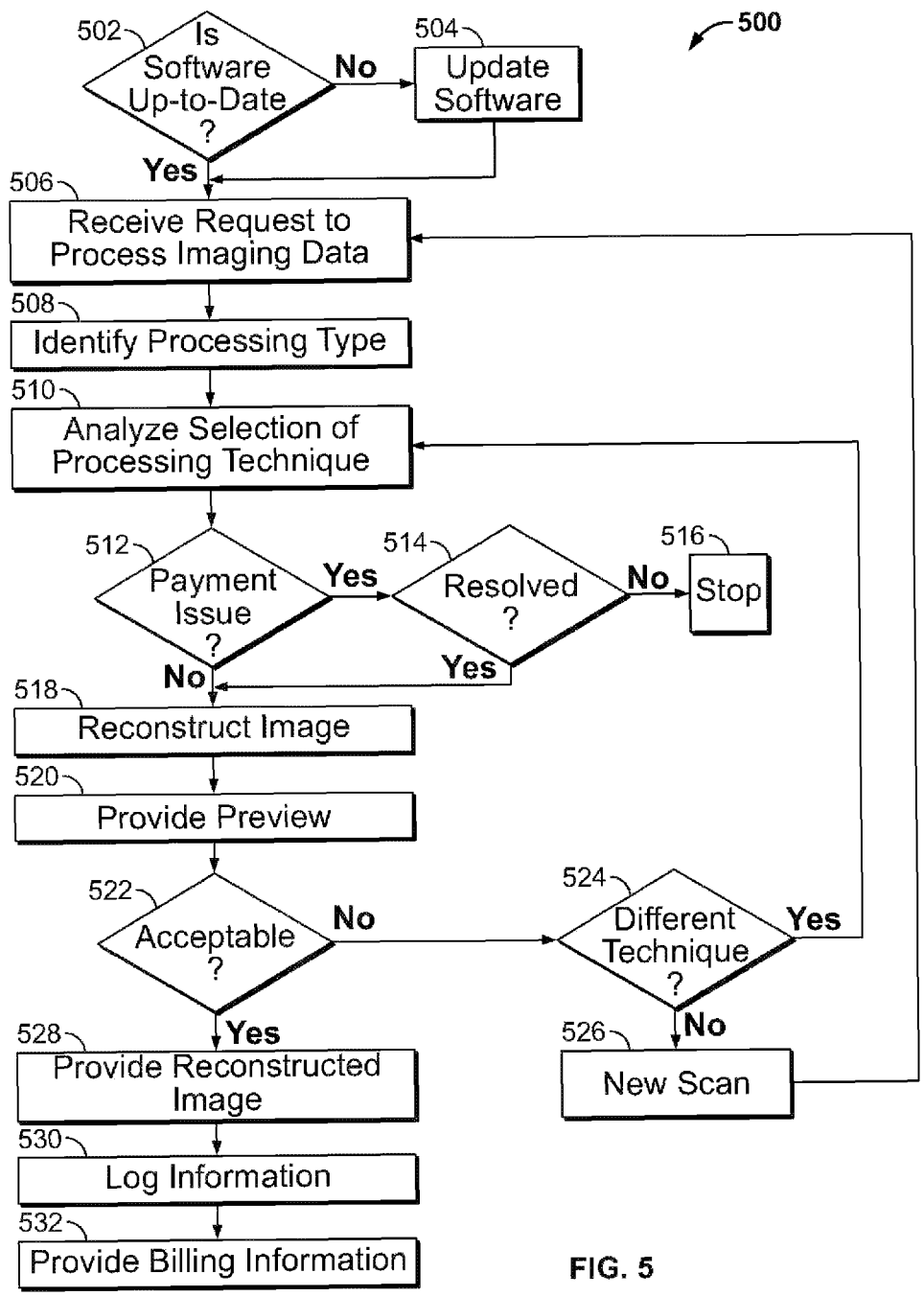
FIG. 5 is a flowchart of a method for reconstructing an image in accordance with various embodiments.

Certain embodiments provide a method for image reconstruction. For example, FIG. 5 provides a flowchart of a method for image reconstruction in accordance with various embodiments. The method 500 may be used, for example, to image a portion of anatomy of interest of a patient using a medical imaging technique such as SPECT or PET. In other embodiments, different medical imaging techniques, or combinations of techniques, may be used. In various embodiments, certain steps may be omitted or added, certain steps may be combined, certain steps may be performed simultaneously, or concurrently, certain steps may be split into multiple steps, certain steps may be performed in a different order, or certain steps or series of steps may be re-performed in an iterative fashion. The method 500 may be performed, for example, in association with systems such as those discussed above.

At 502, the image reconstruction software available at or to a central processing system is analyzed to confirm that the software is up to date. If the software is not up to date, the software is updated to the most current version or release, or state of the art condition available, with any necessary validation for regulatory purposes also performed. In embodiments, at 504, the image reconstruction software is autonomously updated, for example by an update module that is part of the central processing system as discussed above. Such autonomous updates may occur, for example, on a periodic basis (e.g. weekly, monthly, or other).

At 506, a request for processing imaging data is received. Such a request, for example, may include data acquired during a scan. The data may be provided in a standardized format, such as DICOM, or may be provided in a non-standardized format, as discussed above, for example. In alternate embodiments, the data may be provided at a different point in the method. The request and data for example, may be received by a central processing system from a medical scanning system located remotely from the central processing system.

At 508, a processing type is identified. The processing type, for example, may designate a scanning modality (e.g. CT) as well as a level or type of processing (for example, with or without processing to address motion artifacts; or, as another example, an identification of a level of processing intensity based on one or more of an amount of data acquired during a scan or a desire quality level of image). The processing type in embodiments is specified by the user. In embodiments, the central processing system, for example via a user interface, provides a user with prompts identifying available processing techniques along with a billing status of such techniques (e.g. technique is available to user at no additional charge; technique is available for a stated charge; techniques is available for a stated subscription upgrade; technique is available on a trial basis).

At 510, the specified processing technique is analyzed for appropriateness. For example, the central processing system, in embodiments, provides suggestions on a processing technique or techniques based on, for example, benchmarking information identifying processing techniques used by the user and/or a general population of users for a given type of scan. As another example, the central processing system may compare the provided data with threshold requirements for a given processing technique, and, based on a quality or quantity of data provided to the central processing system for image reconstruction, recommend a different processing technique, as appropriate. In embodiments, the comparison and suggestion may be made alternatively or additionally as part of an initial processing technique selection process.

At 512, payment is confirmed. For example, the central processing system may compare user identification information and the type of processing technique requested to reconstruct an image with a subscriber database describing which customers are authorized to have which processing techniques performed. If the user has access to the requested image reconstruction processing technique, the method proceeds to 518. If not, for example, if there is a payment issue, then at 514, the payment issue is addressed. For example, a user may have requested a processing technique to which that particular user does not have access. The user may be offered access to that technique, for example, by paying a one-time fee, or, as another example, by increasing a subscription level. If the payment issue is satisfactorily resolved, for example by a user agreeing to a payment, the method proceeds to 518. If not, the method ends at 516. In embodiments, a user may choose a different technique and return to 508.

At 518, the image is reconstructed. For example, a processing module of the central processing system may utilize a program or programs from a software library module corresponding to the requested or specified processing technique to reconstruct the image using the provided image acquisition data. At 520, a preview of the reconstructed image is presented to the user, for example via a user interface of an output module of the central processing system. The preview may be used, for example, to confirm whether the image will be acceptable at 522. If the requested image will be acceptable, the method proceeds to 528. If the image does not appear acceptable, at 524 a determination may next be made if a different processing technique may render acceptable image quality, or if a new scan will need to be performed. If it is determined that a different processing will address the image quality issue, the method proceeds to 510 to confirm appropriateness of the new technique. If it is determined that an acceptable image may not be reconstructed, a new scan is performed at 526 and the method returns to 506.

At 528, the reconstructed image is provided to a user or requestor. For example, the reconstructed image may be provided to a user at a medical scanning system from which the image acquisition data used to reconstruct the image was received. As another example, the reconstructed image may be provided to an authorized requestor located at a remote workstation.

At 530, information regarding the particular scan is logged and analyzed. As one example, billing information regarding, for example, an identification of the user requesting the image reconstruction, the type of reconstruction technique employed, and a charge associated with the image reconstruction may be tracked. For example, if an image reconstruction was performed using a technique to which the user has free access based on a subscription, the associated charge may be zero. As another example, if an image reconstruction was performed using a technique not available as part of a subscription, the charge may be a one-time fee for the image reconstruction that was paid or agreed to during the requesting of the image reconstruction.

As another example, information regarding characteristics of the scan and/or image reconstruction may be recorded. For example, the scanning equipment used, the type of scan or aspect of a patient scanned, the length of scan, the amount of data acquired during the scan, and/or the processing technique or techniques employed to reconstruct the image may be recorded. Such information may be used to gather cumulative, for example, average, data corresponding to different types of scans performed by users, and used as part of benchmarking analyses. Thus, benchmarking data may be tracked by the central processing system for a much larger population of scans than could be collected by any single on-site processing system. The benchmarking information may be used as a tool to assist users in identifying potential modifications to their scanning techniques (e.g. length of scan or amount of image acquired for a particular scan of a particular aspect of a patient). For example, if a user learns through a benchmarking analysis that the particular user is acquiring scanning information for MRI analysis of knees for a duration of time substantially longer than the average MRI knee scan across all users, that particular user may identify that particular user's MRI scan procedures for further follow up and analysis to potentially shorten the scan duration, if appropriate.

At 532, billing information is provided to a user. The billing information may include a specific charge agreed to during performance of the method 500. As another example, if a performed image reconstruction was covered by a subscription, the billing information may include a notification that the reconstruction was performed for no additional charge. The billing information may also include, for example, information regarding potential alternative image reconstruction processing techniques (for example, an upcoming update) for future consideration for similar scans, and may also include any pertinent pricing information or options regarding such alternative processing techniques.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. For example, a module or system may include a computer processor, controller, or other logic-based device that performs operations based on instructions stored on a tangible and non-transitory computer readable storage medium, such as a computer memory. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A system comprising:
a processing unit located at a first location that is remote from a scanning location at which a remote medical scanning system is located, the processing unit comprising:
an input module configured to communicate with the remote medical scanning system to receive scanning data obtained during a scan performed by the remote medical scanning system, the scanning data acquired by the remote medical scanning system during a scan performed on an object scanned by the remote medical scanning system;
a processing module configured to use the scanning data to reconstruct an image representing the object using a reconstruction technique selected from a plurality of reconstruction techniques available to the processing module, the plurality of techniques including a plurality of sub-groups of techniques, the plurality of sub-groups relating to a corresponding plurality of imaging modalities, wherein the processing module is configured to select the reconstruction technique based on the scanning data, wherein the processing module is configured to autonomously select the reconstruction technique based upon at least one of a quantity or quality of the scanning data received by the input module; and
an output module configured to provide access to the image reconstructed by the processing module to at least one of the remote medical scanning system or a requestor located remotely from the first location.

2. A system in accordance with claim 1, wherein the output module is configured to transmit the image to the remote medical scanning system.

3. A system in accordance with claim 1, wherein the output module is configured to determine if the remote requestor is authorized to view the image, and, if the remote requestor is authorized, to display the image to the remote requestor.

4. A system in accordance with claim 1, further comprising a billing module, the billing module configured to identify a payment required from the at least one of the remote medical scanning system or the requestor located remotely from the first location, the payment corresponding to a type of processing performed to reconstruct the image.

5. A system in accordance with claim 1, further comprising an updating module configured to periodically update software used by the processing module to reconstruct the image.

6. A system in accordance with claim 1, wherein the input module is configured to receive the scanning data in a standardized format, wherein the system may receive and process data from a plurality of remote scanning systems having a corresponding plurality of compatibility types.

7. A system in accordance with claim 1 further comprising a tracking module, the tracking module configured to log a plurality of scans and provide comparative information regarding the plurality of scans.

8. A system in accordance with claim 1, wherein the processing unit is configured to autonomously select and implement the selected reconstruction technique, wherein the selected reconstruction technique is selected based on the quantity of the scanning data, wherein a first, less intensive reconstruction technique is selected for a first amount of data and a second, more intensive reconstruction technique is selected for a second amount of data that is less than the first amount of data.

9. A system in accordance with claim 1, wherein the processing unit is configured to recommend the selected reconstruction technique to a user, wherein the selected reconstruction technique is selected based on the quantity of the scanning data, wherein a first, less intensive reconstruction technique is selected for a first amount of data and a second, more intensive reconstruction technique is selected for a second amount of data that is less than the first amount of data.

10. The system of claim 1, wherein the processing unit is configured to perform a comparison of the quantity of data to a threshold and to select the reconstruction technique based on the comparison of quantity of data to threshold.

11. The system of claim 1, wherein the processing unit configured to suggest the reconstruction technique based on the determined quantity.

12. A method comprising:
receiving, at a processing center located at a first location, from a medical scanning system located at a second location, scanning data acquired during a scan performed by the medical scanning system, wherein the first location and the second location are remote from each other,
selecting, via a processing module of the processing center, a reconstruction technique from a plurality of reconstruction techniques available to the processing module, the plurality of techniques including a plurality of sub-groups of techniques, the plurality of sub-groups relating to a corresponding plurality of imaging modalities, wherein the reconstruction technique is selected based on at least one of a quantity or quality of the scanning data received by the input module;
reconstructing an image at the processing center using the scanning data from the medical scanning system and the selected reconstruction technique; and
providing access to the image reconstructed at the processing center to at least one of the medical scanning system or a requestor located remotely from the processing center.

13. A method in accordance with claim 12 further comprising:
identifying a type of processing to be used for the reconstructing the image, the type of processing corresponding to at least one of a request from the medical scanning system or a type of information provided by the medical scanning system, and
confirming that the medical scanning system has permission for the type of processing identified;
wherein the reconstructing an image is performed responsive to the confirming that the medical scanning system has permission.

14. A method in accordance with claim 12 wherein the providing access to the image reconstructed at the processing center comprises transmitting the image to the remote medical scanning system.

15. A method in accordance with claim 12 wherein the providing access to the image reconstructed at the processing center comprises determining if the remote requestor is authorized to view the image, and, if the remote requestor is authorized, to display the image to the remote requestor.

16. A method in accordance with claim 12 further comprising identifying a payment required from the at least one of the remote medical scanning system or the requestor located remotely from the first location, the payment corresponding to a type of processing performed to reconstruct the image.

17. A method in accordance with claim 12 further comprising periodically updating software used by the processing center for the reconstructing the image.

18. A method in accordance with claim 12 wherein the scanning data is received in a standardized format, wherein the processing center may receive and process data from a plurality of remote scanning systems having a corresponding plurality of compatibility types.

19. A method in accordance with claim 12, wherein the processing center is administered by a first party, and the medical scanning system is administered by a second party that is distinct from the first party.

20. A method in accordance with claim 12 further comprising tracking a plurality of scans and providing comparative information regarding the plurality of scans.

21. A method in accordance with claim 12 further comprising recommending, via the processing module, the reconstruction technique to a user, wherein the selected reconstruction technique is selected based on the quantity of the scanning data, wherein a first, less intensive reconstruction technique is selected for a first amount of data and a second, more intensive reconstruction technique is selected for a second amount of data that is less than the first amount of data.

22. A tangible and non-transitory computer readable medium comprising one or more computer software modules configured to direct a processor to:
   receive, at a processing center located at a first location, scanning data from a medical scanning system located at a second location, the scanning data acquired by the medical scanning system during a scan performed by the medical scanning system, wherein the first location and the second location are remote from each other;
   select, via a processing module of the processing center, a reconstruction technique from a plurality of reconstruction techniques available to the processing module, the plurality of techniques including a plurality of sub-groups of techniques, the plurality of sub-groups relating to a corresponding plurality of imaging modalities, wherein the reconstruction technique is selected based on at least one of a quantity or quality of the scanning data received by the input module;
   reconstruct an image at the processing center using the scanning data from the medical scanning system and the selected reconstruction technique; and
   provide access to the image reconstructed at the processing center to at least one of the medical scanning system or a requestor located remotely from the processing center.

23. A computer readable medium in accordance with claim 22, wherein the computer readable medium is further configured to direct the processor to:
   identify a type of processing to be used to reconstruct the image, the type of processing corresponding to at least one of a request from the medical scanning system or a type of information provided by the medical scanning system;
   confirm that the medical scanning system has permission for the type of processing identified; and
   reconstruct the image responsive to the confirming that the medical scanning system has permission.

24. A computer readable medium in accordance with claim 23 wherein the computer readable medium is further configured to direct the processor to identify a payment required from the at least one of the remote medical scanning system or the requestor located remotely from the first location, the payment corresponding to a type of processing performed to reconstruct the image.

25. A computer readable medium in accordance with claim 22 wherein the computer readable medium is further configured to direct the processor to periodically update software used by the processing center to reconstruct the image.

26. A computer readable medium in accordance with claim 22 wherein the scanning data is received in a standardized format, wherein the processing center may receive and process data from a plurality of remote scanning systems having a corresponding plurality of compatibility types.

27. A computer readable medium in accordance with claim 22 wherein the computer readable medium is further configured to direct the processor to track a plurality of scans and provide comparative information regarding the plurality of scans.

* * * * *